United States Patent
Wu et al.

(10) Patent No.: US 11,306,067 B2
(45) Date of Patent: Apr. 19, 2022

(54) DIPHENYL SUBSTITUTED THIOPHENE-2-AMIDE DERIVATIVES AND PHARMACEUTICAL COMPOSITIONS THEREOF USEFUL AS ANTIMICROBIAL

(71) Applicant: DENOVAMED INC., Toronto (CA)

(72) Inventors: Fan Wu, Toronto (CA); Erhu Lu, Toronto (CA); Shengguo Sun, Toronto (CA); Christopher J. Barden, Toronto (CA)

(73) Assignee: Denovamed Inc., Halifax (CA)

( * ) Notice: Subject to any disclaimer, the term of this patent is extended or adjusted under 35 U.S.C. 154(b) by 5 days.

(21) Appl. No.: 16/975,472

(22) PCT Filed: Mar. 1, 2019

(86) PCT No.: PCT/CA2019/050242
§ 371 (c)(1),
(2) Date: Aug. 25, 2020

(87) PCT Pub. No.: WO2019/169479
PCT Pub. Date: Sep. 12, 2019

(65) Prior Publication Data
US 2021/0017147 A1  Jan. 21, 2021

Related U.S. Application Data

(60) Provisional application No. 62/638,832, filed on Mar. 5, 2018, provisional application No. 62/727,809, filed on Sep. 6, 2018.

(51) Int. Cl.
| | | |
|---|---|---|
| *C07D 333/38* | (2006.01) |
| *C07D 333/34* | (2006.01) |
| *C07D 333/36* | (2006.01) |
| *A61K 31/43* | (2006.01) |
| *A61K 31/7048* | (2006.01) |
| *A61K 38/12* | (2006.01) |

(52) U.S. Cl.
CPC ......... *C07D 333/38* (2013.01); *C07D 333/34* (2013.01); *C07D 333/36* (2013.01); *A61K 31/43* (2013.01); *A61K 31/7048* (2013.01); *A61K 38/12* (2013.01)

(58) Field of Classification Search
CPC ............................ C07D 333/38; C07D 333/34
See application file for complete search history.

(56) References Cited

U.S. PATENT DOCUMENTS

| | | | |
|---|---|---|---|
| 9,012,655 B2 * | 4/2015 | Wu .......................... | A61P 43/00 548/202 |
| 2003/0199570 A1 | 10/2003 | Coghlan et al. | |
| 2006/0264470 A1 | 11/2006 | Barth et al. | |

FOREIGN PATENT DOCUMENTS

| | | |
|---|---|---|
| WO | 1991019708 | 12/1991 |
| WO | 2012116452 | 9/2012 |

* cited by examiner

*Primary Examiner* — Marcos L Sznaidman
(74) *Attorney, Agent, or Firm* — Michael R Williams; Ryan W Dupuis; Ade & Company Inc

(57) ABSTRACT

Compounds or pharmaceutical acceptable salts thereof of Formula (I), in which RM have the meaning described herein and pharmaceutical compositions thereof useful as antimicrobial and/or adjuvant:

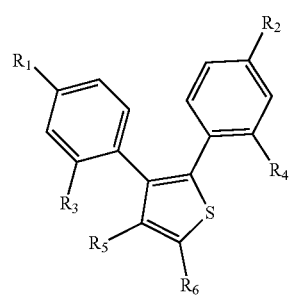

(I)

22 Claims, No Drawings

DIPHENYL SUBSTITUTED THIOPHENE-2-AMIDE DERIVATIVES AND PHARMACEUTICAL COMPOSITIONS THEREOF USEFUL AS ANTIMICROBIAL

CROSS-REFERENCE TO RELATED APPLICATIONS

This application is a 371 of PCT Application CA2019/050242, filed Mar. 1, 2019, which claimed the benefit of U.S. provisional patent 62/727,809, filed Sep. 6, 2018, and U.S. provisional patent 62/638,832, filed Mar. 5, 2018, the contents of which are hereby incorporated by reference.

BACKGROUND

Infection is an invasion of a host organism by a foreign organism, generally to the detriment of normal function in the host. In treating humans and other animals for infection and post-infective inflammatory disease (e.g. septic shock), practitioners usually rely on chemical compounds known to have antibiotic affects, whether antiviral, antibacterial, antifungal, or the like.

Unfortunately, many pathogens have become resistant to current antibiotic treatments. Antibiotic resistance is therefore an increasingly significant clinical issue, calling for novel antibiotics. Especially valuable would be new antimicrobial adjuvant compounds, which, while not necessarily antimicrobial themselves, can increase the potency, efficacy, and/or spectrum of activity of antibiotics when co-administered or given as combination therapy. There is a need for new antimicrobials and new antimicrobial adjuvant compounds.

SUMMARY

The compounds of the present invention are of utility in antimicrobial infections. In some cases, the compounds are themselves antimicrobial. In some cases, the compounds ("antimicrobial adjuvants") have beneficial effects in conjunction with an antimicrobial, reducing the dose of antibiotic required for antimicrobial activity when administered in combination. In some cases, the compounds are both antimicrobial and antimicrobial adjuvants.

In general, in an aspect, compounds of Formula I or pharmaceutically acceptable salts thereof are provided:

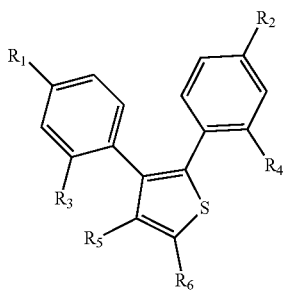

(I)

in which $R_1$ and $R_2$ are each independently fluoro or chloro; $R_3$ and $R_4$ are each independently alkyl; $R_5$ is hydrogen or alkyl; and $R_6$ is amide, sulfonamide, hydroxamic acid, —CH(CF$_3$)OH, or —C(CF$_3$)$_2$OH. Implementations may include one or more of the following. $R_3$ and $R_4$ are each independently methyl, ethyl, or isopropyl. $R_1$ and $R_2$ are each both chloro. $R_3$ and $R_4$ are both methyl. $R_3$ and $R_4$ are both isopropyl. $R_6$ is —CH(CF$_3$)OH and the compound of Formula I is a racemate. $R_6$ is —CH(CF$_3$)OH and the compound of Formula I is the (R) enantiomer. $R_6$ is —CH(CF3)OH and the compound of Formula I is the (S) enantiomer.

In general, in an aspect, a method of treatment of a microbial infection is provided including administering an effective amount of an antimicrobial compound disclosed herein to a patient in need thereof.

In general, in an aspect, a method of treatment of a microbial infection is provided including administering an effective amount of an antimicrobial adjuvant compound disclosed herein and an effective amount of an antimicrobial compound to a patient in need thereof.

Compounds of other formulae are provided as described in the Detailed Description below.

DETAILED DESCRIPTION

Definitions

Unless otherwise defined, terms as used in the specification refer to the following definitions, as detailed below.

The terms "administration" or "administering" compound should be understood to mean providing a compound of the present invention to an individual in a form that can be introduced into that individual's body in an amount effective for prophylaxis, treatment, or diagnosis, as applicable. Such forms may include for example oral dosage forms, injectable dosage forms, transdeinial dosage forms, inhalation dosage forms, and rectal dosage forms.

The term "alkyl" as used herein means a straight or branched chain hydrocarbon containing from 1 to 20 carbon atoms, preferably from 1 to 10 carbon atoms, more preferably 1, 2, 3, 4, 5, or 6 carbons. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "amido" as used herein means an amino, alkylamino, or dialkylamino group appended to the parent molecular moiety through a carbonyl group, as defined herein. Representative examples of amido include, but are not limited to, aminocarbonyl, methylaminocarbonyl, dimethylaminocarbonyl, and ethylmethylaminocarbonyl.

The term "amino" as used herein means a —NH$_2$ group.

The term "carbonyl" as used herein means a —C(=O)— group.

The term "carboxy" as used herein means a —COOH group, which may be protected as an ester group: —COO-alkyl.

The term "cyano" as used herein means a —CN group.

The term "dialkylamino" as used herein means two independent alkyl groups, as defined herein, appended to the parent molecular moiety through a nitrogen atom. Representative examples of dialkylamino include, but are not limited to, dimethylamino, diethylamino, ethylmethylamino, and butylmethylamino.

The term "fluoro" as used herein means —F.

The term "formyl" as used herein means a —C(O)H group.

The term "halo" or "halogen" as used herein means Cl, Br, I, or F.

The term "hydroxy" as used herein means an —OH group.

The term "hydroxy-protecting group" means a substituent which protects hydroxyl groups against undesirable reactions during synthetic procedures. Examples of hydroxy-protecting groups include, but are not limited to, methoxymethyl, benzyloxymethyl, 2-methoxyethoxymethyl, 2-(trimethylsilyl)ethoxymethyl, benzyl, triphenylmethyl, 2,2,2-trichloroethyl, t-butyl, trimethylsilyl, t-butyldimethylsilyl, t-butyldiphenylsilyl, methylene acetal, acetonide benzylidene acetal, cyclic ortho esters, methoxymethylene, cyclic carbonates, and cyclic boronates. Hydroxy-protecting groups are appended onto hydroxy groups by reaction of the compound that contains the hydroxy group with a base, such as triethylamine, and a reagent selected from an alkyl halide, alkyl triflate, trialkylsilyl halide, trialkylsilyl triflate, aryldialkylsilyltriflate, or an alkylchloroformate, $CH_2I_2$, or a dihaloboronate ester, for example with methyliodide, benzyl iodide, triethylsilyltriflate, acetyl chloride, benzylchloride, or dimethylcarbonate. A protecting group also may be appended onto a hydroxy group by reaction of the compound that contains the hydroxy group with acid and an alkyl acetal.

The term "imino" as defined herein means a —C(=NH)— group.

The term "mercapto" as used herein means a —SH group.

The term "nitro" as used herein means a —$NO_2$ group.

The term "nitrogen protecting group" as used herein means those groups intended to protect a nitrogen atom against undesirable reactions during synthetic procedures. Nitrogen protecting groups comprise carbamates, amides, N-benzyl derivatives, and imine derivatives. Preferred nitrogen protecting groups are acetyl, benzoyl, benzyl, benzyloxycarbonyl (Cbz), formyl, phenylsulfonyl, pivaloyl, tert-butoxycarbonyl (Boc), tert-butylacetyl, trifluoroacetyl, and triphenylmethyl (trityl). Nitrogen-protecting groups are appended onto primary or secondary amino groups by reacting the compound that contains the amine group with base, such as triethylamine, and a reagent selected from an alkyl halide, an alkyl triflate, a dialkyl anhydride, for example as represented by (alkyl-O)2C=O, a diaryl anhydride, for example as represented by (aryl-O)2C=O, an acyl halide, an alkylchloroformate, or an alkylsulfonylhalide, an arylsulfonylhalide, or halo-CON(alkyl)2, for example acetylchloride, benzoylchloride, benzylbromide, benzyloxycarbonylchloride, formylfluoride, phenylsulfonylchloride, pivaloylchloride, (tert-butyl-O—C=O)2O, trifluoroacetic anhydride, and triphenylmethylchloride.

The term "oxo" as used herein means (=O).

Unless otherwise indicated, the term "prodrug" encompasses pharmaceutically acceptable esters, carbonates, thiocarbonates, N-acyl derivatives, N-acyloxyalkyl derivatives, quaternary derivatives of tertiary amines, N-Mannich bases, Schiff bases, aminoacid conjugates, phosphate esters, metal salts and sulfonate esters of compounds disclosed herein. Examples of prodrugs include compounds that comprise a biohydrolyzable moiety (e.g., a biohydrolyzable amide, biohydrolyzable carbamate, biohydrolyzable carbonate, biohydrolyzable ester, biohydrolyzable phosphate, or biohydrolyzable ureide analog). Prodrugs of compounds disclosed herein are readily envisioned and prepared by those of ordinary skill in the art. See, e.g., Design of Prodrugs, Bundgaard, A. Ed., Elseview, 1985; Bundgaard, hours., "Design and Application of Prodrugs," A Textbook of Drug Design and Development, Krosgaard-Larsen and hours. Bundgaard, Ed., 1991, Chapter 5, p. 113-191; and Bundgaard, hours., Advanced Drug Delivery Review, 1992, 8, 1-38.

Unless otherwise indicated, the term "protecting group" or "protective group," when used to refer to part of a molecule subjected to a chemical reaction, means a chemical moiety that is not reactive under the conditions of that chemical reaction, and which may be removed to provide a moiety that is reactive under those conditions. Protecting groups are well known in the art. See, e.g., Greene, T. W. and Wuts, P.G.M., Protective Groups in Organic Synthesis (3rd ed., John Wiley & Sons: 1999); Larock, R. C., Comprehensive Organic Transformations (2nd ed., John Wiley & Sons: 1999). Some examples include benzyl, diphenylmethyl, trityl, Cbz, Boc, Fmoc, methoxycarbonyl, ethoxycarbonyl, and pthalimido. Protecting groups include, for example, nitrogen protecting groups and hydroxy-protecting groups.

The term "sulfonyl" as used herein means a —$S(O)_2$— group.

Certain compounds of the present invention may exist as stereoisomers wherein, asymmetric or chiral centers are present. These stereoisomers are "R" or "S" depending on the configuration of substituents around the chiral carbon atom. The temis "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds may be prepared synthetically from commercially available starting materials which contain asymmetric or chiral centers or by preparation of racemic mixtures followed by resolution well known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, incorporated herein by reference for the disclosure of methods for separation and purification of diastereomers or (2) direct separation of the mixture of optical enantiomers on chiral chromatographic columns or (3) fractional recrystallization methods.

Certain compounds of the present invention may exist as cis or trans isomers, wherein substituents on a ring may attached in such a manner that they are on the same side of the ring (cis) relative to each other, or on opposite sides of the ring relative to each other (trans). Such methods are well known to those of ordinary skill in the art, and may include separation of isomers by recrystallization or chromatography. It should be understood that the compounds may possess tautomeric forms, as well as geometric isomers, and that these also constitute an aspect.

It should be noted that a chemical moiety that forms part of a larger compound may be described herein using a name commonly accorded it when it exists as a single molecule or a name commonly accorded its radical. For example, the terms "pyridine" and "pyridyl" are accorded the same meaning when used to describe a moiety attached to other chemical moieties. Thus, for example, the two phrases "XOH, wherein X is pyridyl" and "XOH, wherein X is pyridine" are accorded the same meaning, and encompass the compounds pyridin-2-ol, pyridin-3-ol and pyridin-4-ol.

It should also be noted that names of compounds having one or more chiral centers that do not specify the stereochemistry of those centers encompass pure stereoisomers and mixtures thereof. Moreover, any atom shown in a drawing with unsatisfied valences is assumed to be attached to enough hydrogen atoms to satisfy the valences. In addition, chemical bonds depicted with one solid line parallel to one dashed line encompass both single and double (e.g., aromatic) bonds, if valences permit.

The term "pharmaceutically acceptable excipient", as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

Unless otherwise indicated, a "therapeutically effective amount" of a compound is an amount sufficient to treat a disease or condition, or one or more symptoms associated with the disease or condition. In some embodiments, "treatment" may be determined by comparison to an untreated control.

The term "subject" is intended to include living organisms in which disease may occur. Examples of subjects include humans, monkeys, cows, sheep, goats, dogs, cats, mice, rats, and transgenic species thereof.

The present invention is based, at least in part, on the design of compounds that inhibit acyl carrier protein (ACP) synthase (AcpS), the enzyme responsible for converting apo-ACP into holo-ACP. AcpS is present not only in Gram-positive and -negative bacteria, but also in acid-fast bacteria such as $Mycobacterium\ tuberculosis$, and even in protozoa such as $Plasmodium\ falciparum$. Accordingly, AcpS inhibitors are expected to have deleterious effects on the viability of many microbes. AcpS inhibitors are be expected to have deleterious effects on the maintenance of microbial cell function, including, for example, increased porosity of cell membranes and dysfunction of efflux pumps in such membranes. In some embodiments, a compound is an AcpS inhibitor. The spectrum of activity demonstrated for compounds of the present invention includes many Gram-positive bacteria including Methicillin-resistant $S.\ aureus$, with selected compounds retaining activity against Gram-negative pathogens such as $Ps.\ aeruginosa,\ Ac.\ baumanii$, and $S.\ maltophilia$, etc. Compounds of the present invention with low or no antimicrobial potency against, for example, $Ps.\ aeruginosa$, may have antimicrobial adjuvant ("adjuvant" or "pro-antibiotic") effects when co-administered with antimicrobial compounds such as, for example, colistin, azithromycin, erythromycin, or ampicillin, or with antimicrobial compounds of the present invention.

Though the utility of the compounds disclosed herein does not depend per se on their being AcpS inhibitors, the design effects toward that goal resulted, at least in part, in the discovery of the compounds of the present invention. While not wishing to be bound to a particular theory or hypothesis, the inventors believe that by inhibiting AcpS in a bacterium, the compounds of the present invention interfere with essential cellular functions of lipid metabolism within the bacterium. This interference with bacterial lipid metabolism has the potential to greatly impact the maintenance of bacterial cell membranes, which is expected to result in porous membranes that allow antimicrobial compounds to enter that otherwise would not be able to cross an intact bacterial cell membrane. Moreover, efflux pumps generally present within the bacterial cell membrane are expected to be insufficient to remove antimicrobial compounds at the concentrations possible within a bacterium having a porous membrane. These and other factors may relate to the mechanism of antimicrobial adjuvants described herein.

According to an embodiment, a compound, or prodrug or pharmaceutically acceptable salt thereof, is provided according to one of Formulas I:

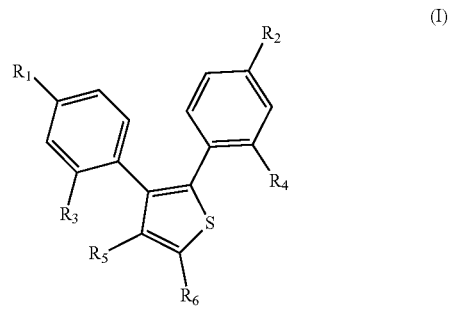

(I)

in which $R_1$ and $R_2$ are each independently fluoro or chloro; $R_3$ and $R_4$ are each independently alkyl; $R_5$ is hydrogen or alkyl; and $R_6$ is amide, sulfonamide, hydroxamic acid, —CH(CF$_3$)OH, or —C(CF$_3$)$_2$OH. In some embodiments, $R_3$ and $R_4$ are each independently methyl, ethyl, or isopropyl. In some embodiments, $R_1$ and $R_2$ are each both chloro. In some embodiments, $R_3$ and $R_4$ are both methyl. In some embodiments, $R_3$ and $R_4$ are both isopropyl. In some embodiments, $R_6$ is —CH(CF$_3$)OH and the compound of Formula I is a racemate. In some embodiments, $R_6$ is —CH(CF$_3$)OH and the compound of Formula I is the (R) enantiomer. In some embodiments, $R_6$ is —CH(CF$_3$)OH and the compound of Formula I is the (S) enantiomer.

According to an embodiment (DNM0650), $R_1$ and $R_2$ are both Cl, $R_3$ and $R_4$ are both isopropyl, $R_5$ is H, and $R_6$ is amide.

According to an embodiment (DNM0652), $R_1$ and $R_2$ are both Cl, $R_3$ and $R_4$ are both methyl, $R_5$ is H, and $R_6$ is amide.

According to an embodiment (DNM0658), $R_1$ and $R_2$ are both Cl, $R_3$ and $R_4$ are both methyl, $R_5$ is H, and $R_6$ is sulfonamide.

According to an embodiment (DNM0755), $R_1$ and $R_2$ are both Cl, $R_3$ and $R_4$ are both methyl, $R_5$ is H, and $R_6$ is —C(CF$_3$)$_2$OH.

According to an embodiment (DNM0703), $R_1$ and $R_2$ are both Cl, $R_3$ and $R_4$ are both methyl, $R_5$ is methyl, and $R_6$ is amide.

According to an embodiment (DNM0693), $R_1$ and $R_2$ are both Cl, $R_3$ and $R_4$ are both isopropyl, $R_5$ is H, and $R_6$ is hydroxamic acid.

According to an embodiment (DNM0760), $R_1$ and $R_2$ are both Cl, $R_3$ and $R_4$ are both methyl, $R_5$ is methyl, and $R_6$ is —C(CF$_3$)$_2$OH.

According to an embodiment (DNM0764), $R_1$ and $R_2$ are both Cl, $R_3$ and $R_4$ are both methyl, $R_5$ is methyl, and $R_6$ is —CH(CF$_3$)OH.

According to another embodiment, the compound is DNM0650, wherein R1 and R2 are both Cl, R3 and R4 are both isopropyl, R5 is H, and R6 is amide; DNM0652, wherein R1 and R2 are both Cl, R3 and R4 are both methyl, R5 is H, and R6 is amide; DNM0658, wherein R1 and R2 are both Cl, R3 and R4 are both methyl, R5 is H, and R6 is sulfonamide; DNM0755, wherein R1 and R2 are both Cl, R3 and R4 are both methyl, R5 is H, and R6 is —C(CF$_3$)$_2$OH; DNM0703, wherein R1 and R2 are both Cl, R3 and R4 are both methyl, R5 is methyl, and R6 is amide; DNM0693, wherein R1 and R2 are both Cl, R3 and R4 are both isopropyl, R5 is H, and R6 is hydroxamic acid; DNM0760, wherein R1 and R2 are both Cl, R3 and R4 are both methyl, R5 is methyl, and R6 is —C(CF$_3$)$_2$OH; or DNM0764, wherein R1 and R2 are both Cl, R3 and R4 are both methyl, R5 is methyl, and R6 is —CH(CF$_3$)OH. According to an embodiment, a method of treatment of a microbial infection is provided comprising administering an effective amount of an antimicrobial compound as described herein to a patient in need thereof. In some embodiments, the microbial infection is substantially caused by Gram-positive bacteria. In some embodiments, the microbial infection is substantially caused by *Enterococcus* sp. In some embodiments, the microbial infection is substantially caused by *Staphylococcus* sp. In some embodiments, the microbial infection is substantially caused by *Bacillus* sp. In some embodiments, the microbial infection is substantially caused by *Staphylococcus epidennidis, Staphylococcus aureus* (including methicillin-resistant *Staphylococcus aureus* [MRSA]), *Enterococcus* sp. (including vancomycin-resistant *Enterococcus* [VRE]), *Streptococcus* sp., or *Bacillus* sp. To say that a microbial infection is "substantially caused" by a particular bacterium or species thereof indicates that the given bacterial genus or species is thought to be primarily responsible for the pathology, epidemiology, or symptom profile of the microbial infection and does not rule out the presence of other bacterial species (e.g., benignly colonizing bacteria). In some embodiments, the microbial infection is skin and skin structure infection of ulcers, wound infections, diabetic foot infections, osteomyelitis, pneumonia, anthrax infection, impetigo or secondarily-acquired traumatic lesions, gasteroenteritis, meningitis, pneumonia, gonorrhea, peptic ulcers, nosocomial infections, or blood-stream infection, among others. In some embodiments, the described antimicrobial agents are used as medicinal compounds, for example, for treating humans, or as veterinary compounds, for example, for treating animals, poultry, livestock and the like, as well as in aquaculture and agricultural applications.

According to an embodiment, a method of treatment of a microbial infection is provided comprising administering an effective amount of an antimicrobial adjuvant compound as described herein and an effective amount of an antimicrobial compound to a patient in need thereof. In some embodiments, the antimicrobial adjuvant compound is itself antimicrobial to some extent. Thus, combinations are possible, not only of compounds of the present invention with each other, but also between a compound of the present invention and a known antibacterial compound. In some embodiments, the microbial infection is skin and skin structure infection of ulcers, wound infections, diabetic foot infections, osteomyelitis, pneumonia, impetigo or secondarily-acquired traumatic lesions, gasteroenteritis, meningitis, pneumonia, septicaemia, urinary tract infections, gonorrhea, peptic ulcers, nosocomial infections, blood-stream infection, brucellosis, campylobacteriosis, Cat Scratch fever, cholera, legionellosis, leptospirosis, Lyme disease, melioidosis, meningitis, pertussis, plague, salmonellosis, shigellosis, syphilis, tularemia, typhoid fever, or urinary tract infection. An effective amount of one or more of the above-described antimicrobials may be used in the preparation of a medicament as described above for the treatment of a disease, disorder or condition caused by a pathogenic bacteria selected from the group including but by no means limited to *Escherichia, Klebsiella, Salmonella, Pseudomonas, Neisseria, Legionella, Haemophilus, Campylobacter, Helicobacter* and *Shigella*.

In another embodiment, there is provided a method of manufacturing a medicament for treating a microbial infection comprising admixing an antimicrobial compound as described herein with a suitable excipient.

In other embodiments, there is provided the use of an antimicrobial compound as described herein for treating a microbial infection.

In another embodiment, there is provided a method of manufacturing a medicament for treating a microbial infection comprising admixing an antimicrobial adjuvant as described herein with a suitable antimicrobial compound.

In other embodiments, there is provided the use of an antimicrobial adjuvant as described herein for treating a microbial infection. In some embodiments, the antimicrobial adjuvant is used with or coadministered with an antimicrobial compound.

According to an embodiment, a pharmaceutical composition is provided comprising a compound of the present invention and a pharmaceutically acceptable excipient.

The microbial infection may be substantially caused by one or more Gram-positive bacteria.

The microbial infection may comprise a Staphylococcal infection.

The microbial infection may comprise Enterococcal infection.

The microbial infection may comprise *Bacillus* infection.

The microbial infection may be substantially caused by a bacterial species selected from the group consisting of *Staphylococcus aureus, Staphylococcus epidermidis, Enterococcus faecalis, Enterococcus faecium, Bacillus cereus*, and *Streptococcus* sp.

Alternatively, the microbial infection is substantially caused by Gram-negative bacteria.

The microbial infection may be polymicrobial.

The microbial infection may be substantially caused by *Pseudomonas aeruginosa*. The microbial infection may be substantially caused by *Klebsiella pneumoniae*. The microbial infection may be substantially caused by *Acinetobacter baumannii*.

It is of note that the antimicrobials or antimicrobial adjuvants may be prepared or formulated to be administered in a variety of ways, for example, topically, orally, intravenously, intramuscularly, subcutaneously, intraperitoneally, intranasally or by local or systemic intravascular infusion using means known in the art and as discussed below. Compounds of the present invention may be used, for example, to treat infections caused by Gram negative bacteria such as *E. coli* and/or Gram positive bacteria such as *S. aureus*. In some embodiments, compounds have antimicrobial effects against antibiotic-resistant strains such as, for example, methicillin-resistant *S. aureus* (MRSA). In some embodiments, compounds have antimicrobial effects against *Mycobacterium tuberculosis*.

The antimicrobial or antimicrobial adjuvant compounds may be arranged to be delivered at a concentration of about 1 nM to about 50 mM; or 10 nM to about 50 mM; or 100 nM to about 50 mM; or 1 µM to about 50 mM; or 10 µM to 50 mM or 100 µM to 50 mM. As will be appreciated by one of skill in the art, this may be the "effective amount," that is, a sufficient dosage is administered such that a concentration within one of the envisioned ranges is attained at the required site. In some antimicrobial embodiments, the effective amount will be informed at least in part by the minimum inhibitory concentration of the compound required to exhibit bacteriostatic or bacteriocidal effects against the pathogen of interest. In some antimicrobial adjuvant embodiments, the effective amount will be informed at least in part by the approximate minimum concentration required to produce the desired adjuvant effect with a predetermined known antibiotic against the pathogen of interest. In some embodiments, the effective amount will be calibrated so as to produce a serum level of over ten times the MIC, or over five times the MIC, or over three times the MIC, or at the MIC in a subject suffering from an infection. In some embodiments, the effective amount will be calibrated so as to produce an in situ concentration of over ten times the MIC, or over five time the MIC, or over three times the MIC, or at the MIC.

An effective amount of one of the compounds can be employed in pure form or, where such forms exist, in pharmaceutically acceptable salt form. Alternatively, the compound can be administered as a pharmaceutical composition containing the compound of interest in combination with one or more pharmaceutically acceptable carriers. It will be understood, however, that the total daily usage of the compounds and compositions will be decided by the attending physician within the scope of sound medical judgment. The specific effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; the risk/benefit ratio; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of the present invention as administered to a human or lower animal may range from about 0.0003 to about 30 mg/kg of body weight. For purposes of oral administration, more preferable doses can be in the range of from about 0.0003 to about 1 mg/kg body weight. If desired, the effective daily dose can be divided into multiple doses for purposes of administration; consequently, single dose compositions may contain such amounts or submultiples thereof to make up the daily dose. For oral administration, the compositions are preferably provided in the form of tablets containing about 1.0, about 5.0, about 10.0, about 15.0, about 25.0, about 50.0, about 100, about 250, or about 500 milligrams of the active ingredient.

For best results, whether a particular compound is antimicrobial or an antimicrobial adjuvant with respect to the pathogen of interest (and in the case of adjuvants, with respect to the antimicrobial compound being used) would generally be ascertained by a number of microbiological methods known in the art, including for example, the methods disclosed in the Examples. It is well understood in the art that while every "antimicrobial" compound has an antimicrobial effect against at least one pathogen at one or more effective amounts, antimicrobial compounds vary as to their spectrum and/or potency of activity. Moreover, while every "antimicrobial adjuvant" compound has an adjuvant effect in conjunction with at least one antimicrobial compound against at least one pathogen at one or more effective amounts of both antimicrobial compound and adjuvant, antimicrobial adjuvant compounds vary as to their spectrum, potency of activity, and/or compatibility with particular antimicrobial compounds. As will be apparent to one knowledgeable in the art, the total dosage will vary according to many factors, including but by no means limited to the weight, age and condition of the individual or patient.

In some embodiments, one or more of the antimicrobial compounds may be co-administered with one or more known antibiotics. In some embodiments, one or more of the antimicrobial adjuvant compounds my be co-administered with one or more antimicrobial compounds; in which case the total effective amount of antimicrobial compound may be less than would otherwise be required in the absence of antimicrobial adjuvant, e.g. ~8 times less, or ~16 times less, or ~32 times less, or ~64 times less, or ~125 times less, or ~250 times less. In some embodiments, the antimicrobial adjuvant compounds are not themselves antimicrobial. In some embodiments, the antimicrobial adjuvant compounds are themselves antimicrobial. In some embodiments, one or more of the antimicrobial adjuvant compounds may be combined with one or more antimicrobial compounds in a single dosage form. In some embodiments, the antimicrobial compound is an antimicrobial compound of the present invention. In some embodiments, the antimicrobial compound is a known antimicrobial compound such as, for example, almecillin, amdinocillin, amikacin, amoxicillin, amphomycin, amphotericin B, ampicillin, azacitidine, azaserine, azithromycin, azlocillin, aztreonam, artemisinin, allopurinol, amicacin, aminoglycosides, amphotericin B, ampicillin, ansamycins, anthracyclines, antimycotics, azithromycin, bacampicillin, bacitracin, benzyl penicilloylpolylysine, bleomycin, brefeldin A, butoconazole, candicidin, capreomycin, carbenicillin, cefaclor, cefadroxil, cefamandole, cefazoline, cefdinir, cefepime, cefixime, cefinenoxime, cefinetazole, cefodizime, cefonicid, cefoperazone, ceforanide, cefotaxime, cefotetan, cefotiam, cefoxitin, cefpiramide, cefpodoxime, cefprozil, cefsulodin, ceftazidime, ceftibuten, ceftizoxime, ceftriaxone, cefuroxime, cephacetrile, cephalexin, cephaloglycin, cephaloridine, cephalothin, cephapirin, cephradine, chloramphenicol, cilastatin, cinnamycin, ciprofloxacin, clarithromycin, clavulanic acid, clindamycin, clioquinol, cloxacillin, colistimethate, colistin, cyclacillin, cycloserine, cyclosporine, cyclo-(Leu-Pro), camptothecin, cefataxime, cephalexin, cephalosporins, chalcomycin, chartreusin, chlorotetracyclines, chlorothricin, chrymutasins, chrysomicin M, chrysomicin V, clomocyclines, dactinomycin, dalbavancin, dalfopristin, daptomycin, daunorubicin, demeclocycline, detorubicin, dicloxacillin, dihydrostreptomycin, dirithromycin, doxorubicin, doxycycline, ellipticines, elsamicin, epirubicin, erythromycin, eveminomycin, filipins, fluconazoles, fungichromins, fusidic acid, floxacillin, fosfomycin, gentamycin, gilvocarin, griseofulvin, griseoviridin, guamecyclines, gemifloxacin, gramicidin, hetacillin, idarubicin, imipenem, iseganan, ivermectin, ilosamides, itraconazoles, kanamycin, laspartomycin, linezolid, loracarbef, lankamycin, lincomycin, magainin, meclocycline, meropenem, methacycline, mezlocillin, minocycline, mitomycin, moenomycin, moxalactam, moxifloxacin, mycophenolic acid, macrolides, methicillins, mitoxantrone, nafcillin, natamycin, neomycin, netilmicin, niphimycin, nitrofurantoin, novobiocin, nalidixic acid, norfloxin, nystatin, nystatins, ofloxacin, oleanomycin, oxytetracyline, paromomycin, penicillamine, phenethicillin, piperacillin, plicamycin, pristinamycin, pecilocin, penicillins, pesticides, phosphomycin, pimarcin, platensimycin, polyenes, polymyxin B, polymyxin E, quinupristin, quinolones, ravidomycin, reserpines, rifamycin, ristocetins A and B, rifabutin, rifampin, rifamycin, rolitetracycline, sisomycin, spiramycin, spironolactone, sulfacetamide sodium, sulphonamide, spectrinomycin, streptomycin, streptozocin, sulbactam, sultamicillin, tacrolimus, tazobactam, teicoplanin, telithromycin, teramycins, tetracyclines, thiamphenicols, thiolutins, tobramycin, tyrothricin, ticarcillin, tigecycline, tobramycin, troleandomycin, tunicamycin, tyrthricin, vancomycin, vidarabine, viomycin, virginiamycin, and wortmannins; the presence of a plural item in the foregoing list meaning to refer to one or more members of a family of antibiotics known in the art by that name. Which compound or compounds should be co-administered or compounded in combination with compounds of the present invention depends on a number of factors, including but not necessarily limited to the efficacy of the agent or agents in the absence of antimicrobial adjuvant compounds, the mechanism of action of the compound(s), the identity of the pathogen causing or potentiating the sick condition, and/or the severity of the sick condition in the subject.

The pharmaceutical compositions can be formulated for oral administration in solid or liquid form, for parenteral intravenous, subcutaneous, intramuscular, intraperitoneal, intra-arterial, or intradermal injection, for or for vaginal, nasal, topical, or rectal administration. Pharmaceutical compositions of the present invention suitable for oral administration can be presented as discrete dosage forms, e.g., tablets, chewable tablets, caplets, capsules, liquids, and flavored syrups. Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

Parenteral dosage forms can be administered to patients by various routes including subcutaneous, intravenous (including bolus injection), intramuscular, and intraarterial. Because their administration typically bypasses patients' natural defenses against contaminants, parenteral dosage forms are specifically sterile or capable of being sterilized prior to administration to a patient. Examples of parenteral dosage forms include solutions ready for injection, dry products ready to be dissolved or suspended in a pharmaceutically acceptable vehicle for injection, suspensions ready for injection, and emulsions. Pharmaceutical compositions for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants. These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof. If desired, and for more effective distribution, the compounds can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations also are prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of materials which can be useful for delaying release of the active agent can include polymeric substances and waxes.

Dosage forms for topical administration may include powders, sprays, ointments and inhalants. A compound of the present invention can be mixed under sterile conditions with a pharmaceutically acceptable carrier and any needed preservatives, buffers or propellants which may be required. Opthalmic formulations, eye ointments, powders and solutions are contemplated as being within the scope of this invention. Aqueous liquid compositions comprising compounds also are contemplated.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents. Dosage forms for topical or transdermal administration of a compound of this invention include ointments, pastes, creams, lotions, gels, powders, solutions, sprays, inhalants or patches. A desired compound is admixed under sterile conditions with a pharmaceutically acceptable carrier and any needed preservatives or buffers as may be required. Ophthalmic formulation, ear drops, eye ointments, powders and solutions are also contemplated as being within the scope of this invention. The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds, stabilizers, preservatives, and the like. The preferred lipids are the natural and synthetic phospholipids and phosphatidylcholines (lecithins) used separately or together. Methods to form liposomes are known in the art. See, for example, Prescott, Ed., Methods in Cell Biology, Volume XIV, Academic Press, New York, N.Y., (1976), p 33 et seq.

In some embodiments, one or more of the antimicrobials or antimicrobial adjuvants at concentrations or dosages discussed above may be combined with a pharmaceutically or pharmacologically acceptable carrier, excipient or diluent, either biodegradable or non-biodegradable. Exemplary examples of carriers include, but are by no means limited to, for example, poly(ethylene-vinyl acetate), copolymers of lactic acid and glycolic acid, poly(lactic acid), gelatin, collagen matrices, polysaccharides, poly(D,L lactide), poly(malic acid), poly(caprolactone), celluloses, albumin, starch, casein, dextran, polyesters, ethanol, mathacrylate, polyurethane, polyethylene, vinyl polymers, glycols, mixtures thereof and the like. Standard excipients include gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethycellulose phthalate, noncrystalline cellulose, magnesium aluminum silicate, triethanolamine, polyvinyl alcohol, polyvinylpyrrolidone, sugars and starches.

As will be apparent to one knowledgeable in the art, specific carriers and carrier combinations known in the art may be selected based on their properties and release characteristics in view of the intended use. Specifically, the carrier may be pH-sensitive, thermo-sensitive, thermo-gelling, arranged for sustained release or a quick burst. In some embodiments, carriers of different classes may be used in combination for multiple effects, for example, a quick burst followed by sustained release.

In other embodiments, one or more of the antimicrobials or antimicrobial adjuvants at concentrations or dosages described above may be encapsulated for delivery. Specifically, the compounds may be encapsulated in biodegradable microspheres, microcapsules, microparticles, or nanospheres. The delivery vehicles may be composed of, for example, hyaluronic acid, polyethylene glycol, poly(lactic acid), gelatin, poly(E-caprolactone), or a poly(lactic-glycolic) acid polymer. Combinations may also be used, as, for example, gelatin nanospheres may be coated with a polymer of poly(lactic-glycolic) acid. As will be apparent to one knowledgeable in the art, these and other suitable delivery vehicles may be prepared according to protocols known in the art and utilized for delivery of the compounds.

It is of note that the above described antimicrobials may be combined with permeation enhancers known in the art for improving delivery. Examples of permeation enhancers include, but are by no means limited to those compounds described in U.S. Pat. Nos. 3,472,931; 3,527,864; 3,896,238; 3,903,256; 3,952,099; 4,046,886; 4,130,643; 4,130,667; 4,299,826; 4,335,115; 4,343,798; 4,379,454; 4,405,616; 4,746,515; 4,788,062; 4,820,720; 4,863,738; 4,863,970; and 5,378,730; British Pat. No. 1,011,949; and Idson, 1975, J. Pharm. Sci. 64:901-924.

A "pharmaceutically acceptable salt" includes a salt that retains the desired biological activity of the parent antimicrobial or antimicrobial adjuvant compound and does not impart any undesired toxicological effects. Examples of such salts are salts of acids such as hydrochloric acid, hydrobromic acid, sulfuric acid, phosphoric acid, nitric acid, and the like; acetic acid, oxalic acid, tartaric acid, succinic acid, malic acid, benzoic acid, pamoic acid, alginic acid, methanesulfonic acid, naphthalenesulfonic acid, and the like. Also included are salts of cations such as sodium, potassium, lithium, zinc, copper, barium, bismuth, calcium, and the like; or organic cations such as trialkylammonium. Combinations of the above salts are also useful. It is to be understood that a compound disclosed herein in a salt-free form and analogous compound in a pharmaceutically acceptable salt form both compounds of the present invention. Additionally, prodrugs, e.g. esters of the compounds disclosed herein, are compounds of the present invention. The preparation and use of acid addition salts, carboxylate salts, amino acid addition salts, and zwitterion salts of compounds of the present invention may also be considered pharmaceutically acceptable if they are, within the scope of sound medical judgment, suitable for use in contact with the tissues of humans and lower animals without undue toxicity, irritation, allergic response, and the like, are commensurate with a reasonable benefit/risk ratio, and are effective for their intended use. Such salts may also include various solvates and hydrates of the compound of the present invention.

In some embodiments, the described antimicrobial compounds used as medicinal compounds, for example, for treating humans, or as veterinary compounds, for example, for treating animals, poultry, livestock and the like, as well as in aquaculture and agricultural applications.

While various embodiments have been described above, it will be recognized and understood that modifications may be made therein, and the appended claims are intended to cover all such modifications which may fall within the spirit and scope.

Certain embodiments will now be illustrated using examples.

Example 1

Synthesis of Compounds

Compounds were synthesized from commercially available reagents according to the following schemes:

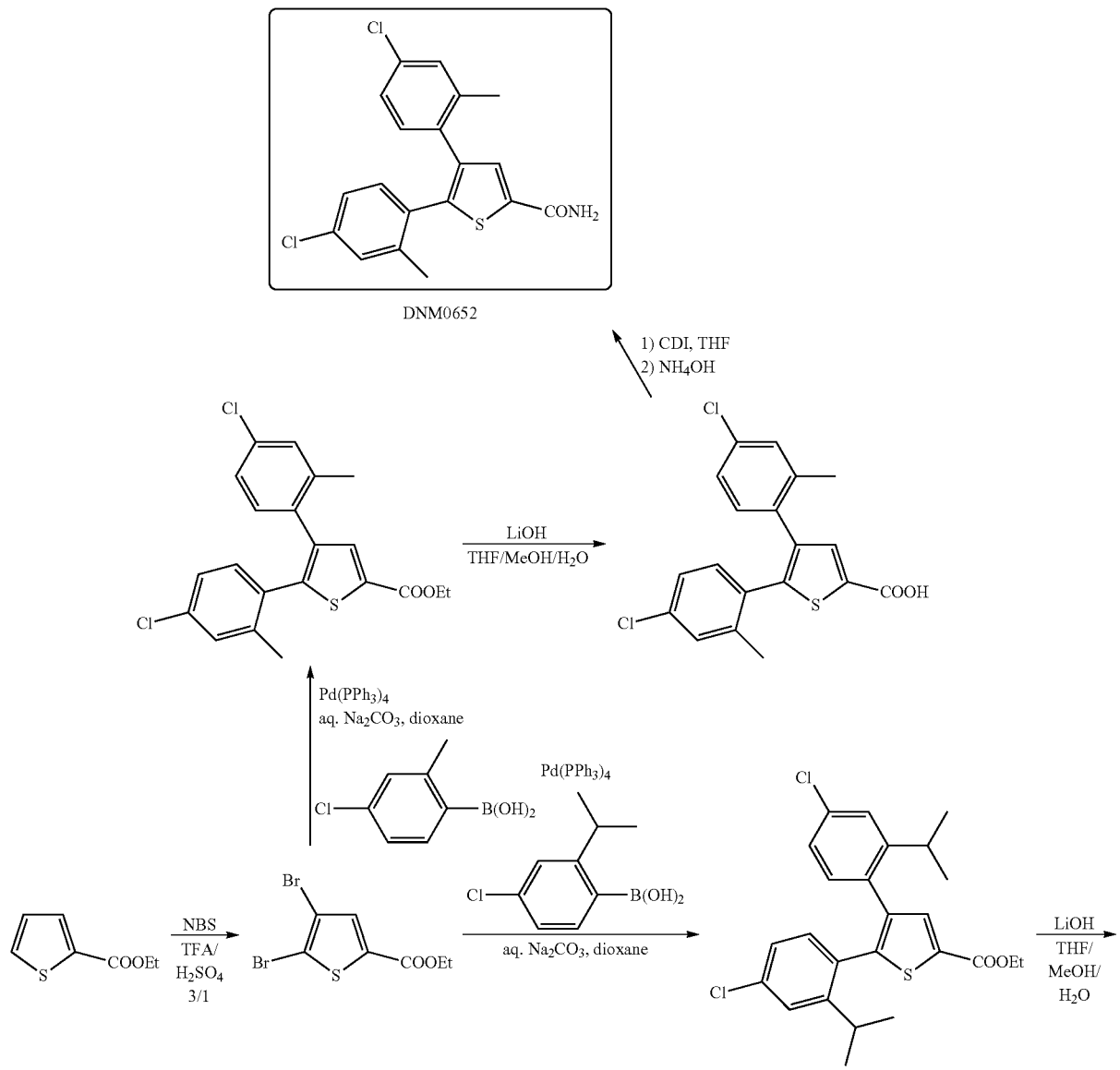

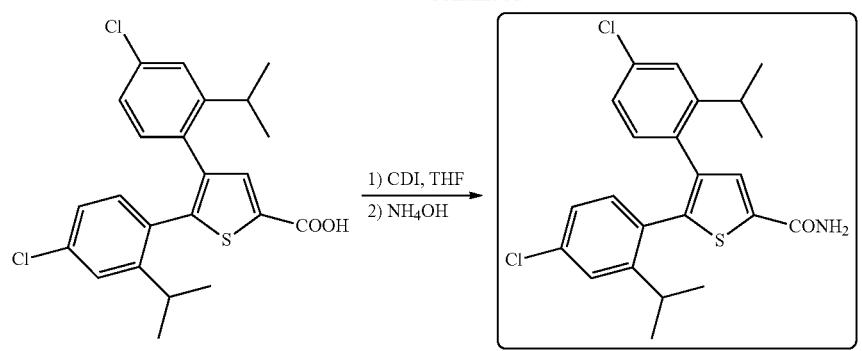
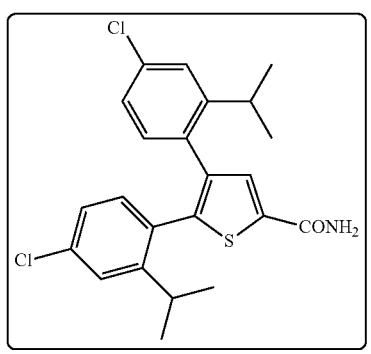
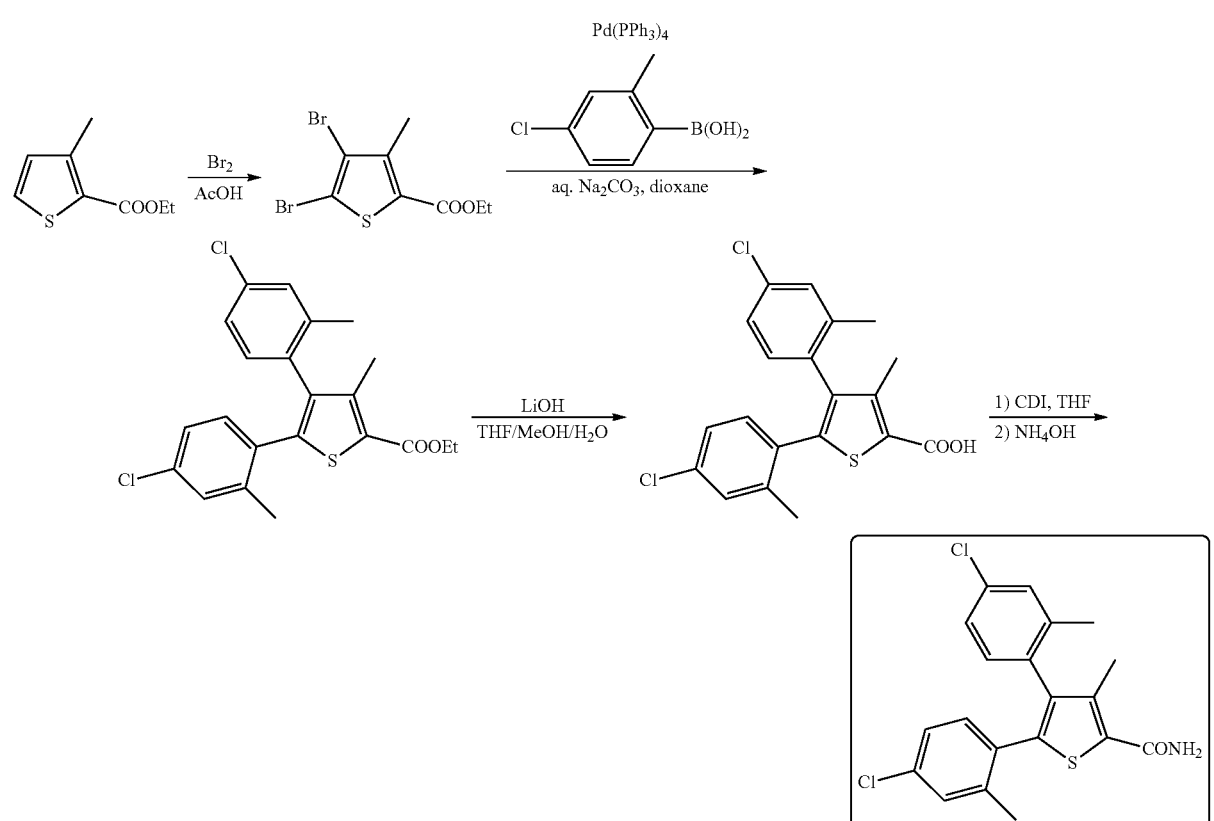

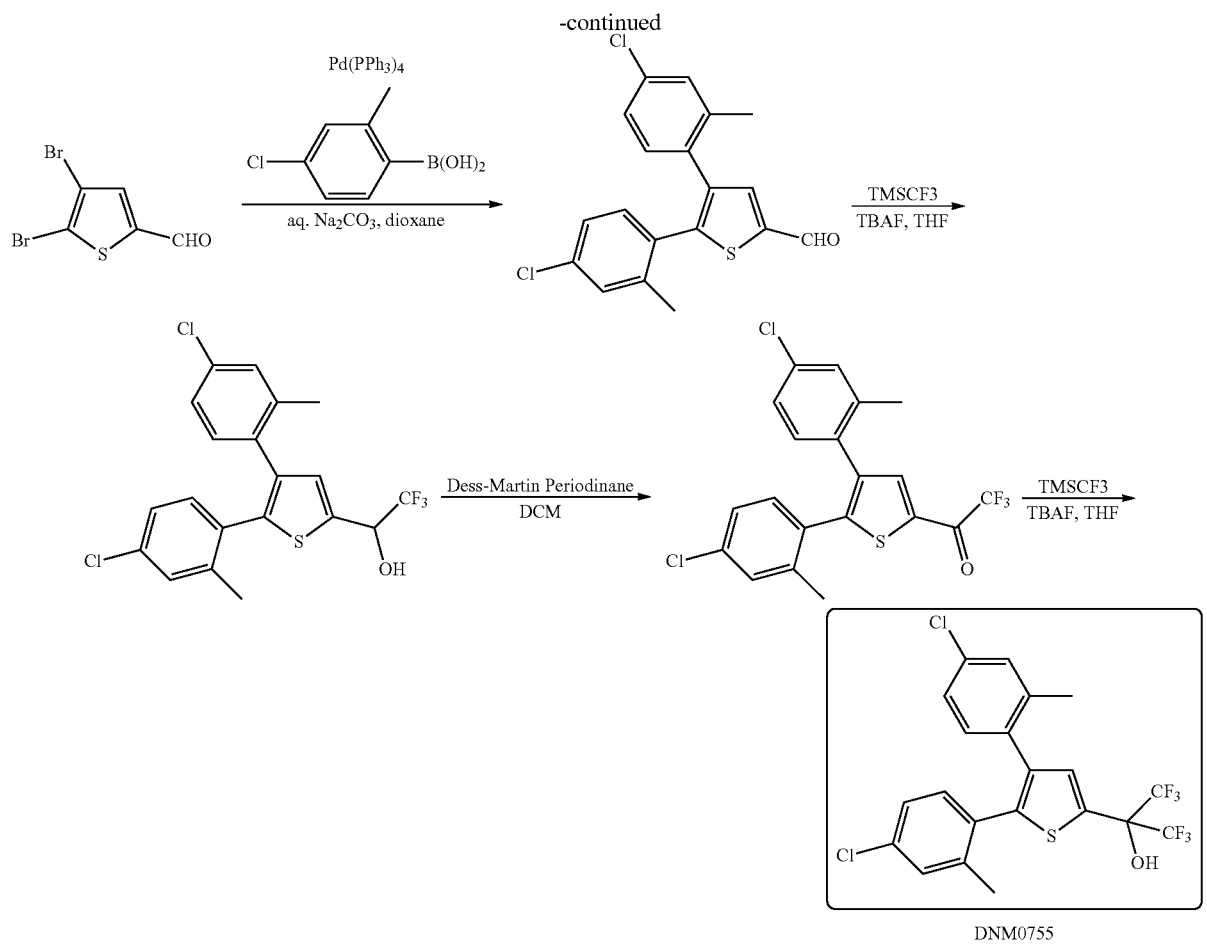

Synthesis of DNM0764 can be accomplished starting with a methylated version of the starting material shown above and proceeding through the palladium coupling and TMSCF3 steps; reacting DNM0764 through the Dess-Martin and further TMSCF3 step can produce DNM0760.

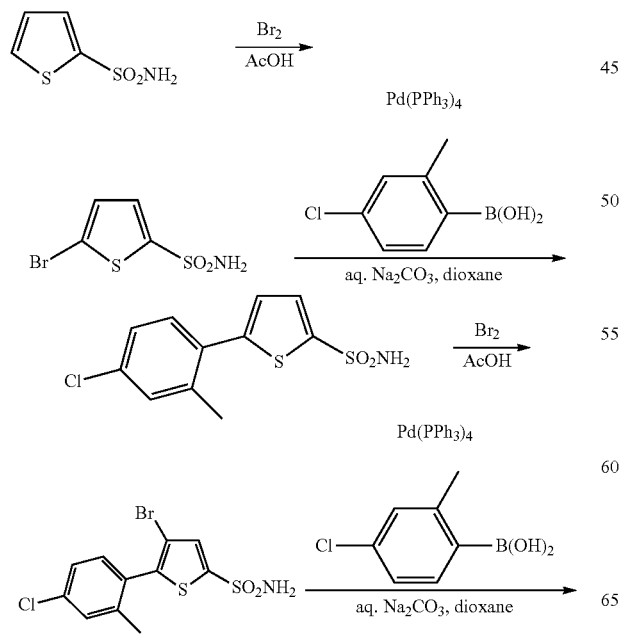

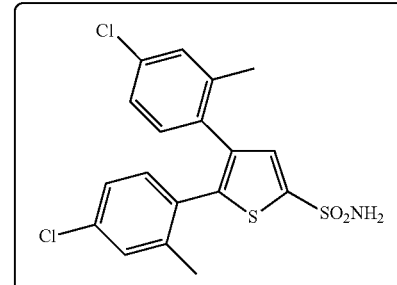

DNM0658

Example 2

Measurement of AcpS Inhibition

Materials

[³H]Acetyl-CoA was mixed as 1 volume of Perkin Elmer NET290 radiolabeled stock (e.g. 0.1 mCi/ml, 3.7 Ci/mmol in Na-acetate, pH 4.5-5.0=27 µM) with 1.2 volumes of 1 mM unlabelled acetyl-CoA (Sigma). Trichloroacetic acid was prepared as a 10% w/v solution. Bovine serum albumin was prepared as a 25 mg/ml solution in water. DTT was prepared as a 50 mM solution in water.

Procedure

1. A standard reaction contained the following in a total volume of 10 μl:

| Stock reagents | Volume (μl) | Final concentration |
|---|---|---|
| 1M Na-phosphate, pH 7 | 0.5 | 50 mM |
| 0.1M MgCl$_2$ | 1 | 10 mM |
| 50 mM DTT | 1 | 5 mM |
| apo-acyl carrier protein (ACP) | 4.4 μg | 50 μM |
| AcpS enzyme | ~0.06 μg | |
| 570 μM [$^3$H] Acetyl-CoA | 1 | 57 μM |
| Test compound | 0.5 | predetermined μM e.g., 50 |
| Dilute with H$_2$O to 10 μl | | |

2. Tubes were incubated at RT. [$^3$H]acetyl-CoA was added last to start the reaction. To stop the reaction, 2 μl was removed to a 1.5-ml microfuge tube containing 800 μl cold 10% TCA. Up to four time points were collected for each reaction, e.g. at 5 min, 10 min, 30 min, and 60 min.
3. 20 μl of 25 mg/ml BSA was added to each tube, mixed and incubated on ice for 10 min, then centrifuged at 12,000 g for 5 min to form a pellet. Supernatant was removed using P1000.
4. Each pellet was washed twice with 800 μl of cold 10% TCA each time, then centrifuged at 12,000 g for 5 min after each wash. The supernatant was discarded.

Each pellet was resuspended in 50 μl of formic acid. The suspension was transferred to a scintillation vial and radioactivity was measured in 2 ml of liquid scintillation cocktail.

The random (stochastic) error in scintillation counting is proportional to the square root of the counts (not dpm) accumulated in the counting period; i.e. 10% for 100, 3.3% for 1,000, 1% for 10,000, etc. Provided radioactive counts (dpm) are in the thousands, the assay provides useful data. Results are reported in terms of % activity with respect to the blank-substracted counts for working substrate. A % activity of less than about 40% is indicative of AcpS enzyme inhibition by the test compound at that concentration. For results, see the table below.

Example 3

Measurement of Minimum Inhibitory Concentrations (MICs)

Susceptibilities to the compounds were determined using the National Committee for Clinical Laboratory Standards (NCCLS) M7-A6 broth microdilution method. Cation-adjusted Mueller-Hinton broth (Ca$^{2+}$, 25 μg/mL; Mg$^{2+}$, 12.5 μg/mL) microdilution panels were prepared to contain antimicrobial doubling dilution concentrations of an appropriate range. DMSO (dimethylsulfoxide) controls were incorporated into the panel to mimic the quantity of DMSO used in dissolving some of the compounds at the higher concentrations. Each final panel well volume was 100 μL with a bacterial inoculum of 5×10$^5$ CFU (colony forming units)/mL. Panels were read following 16 to 20 h of incubation at 35 degrees Celsius in ambient air. The MIC (minimum inhibitory concentration) was defined as the lowest concentration of antimicrobial inhibiting visible growth.

The following table indicates results of experiments for compounds demonstrating AcpS inhibition and/or antimicrobial effects:

| Compound ID | % AcpS activity at 50 uM | MIC MRSA (uM) | MIC E coli (uM) |
|---|---|---|---|
| DNM0650 | | 2 | |
| DNM0652 | 49.7 | 4 | 60 |
| DNM0658 | 49.9 | 2 | |
| DNM0755 | 55.2 | 15 | |
| DNM0703 | 46.9 | 4 | |
| DNM0693 | 35.9 | 125 | |
| DNM0760 | 56.2 | 8 | |
| DNM0764 | 44.0 | 4 | |

Example 4

Measurement of Combination MICs for Antibiotic Adjuvant Potential

The MIC of colistin was determined against the bacteria specified below, by itself or in the presence of 1 ug/ml or 10 ug/ml of a compound disclosed herein (nd=not determined):

| Combination measured | E. coli ATCC 25922 | Klebsiella pneumoniae (Colistin Sensitive) MMX214 | Klebsiella pneumoniae (Colistin Resistant) MMX8390 | Pseudomonas aeruginosa ATCC 27853 | Acinetobacter Baumannii ATCC 19606 |
|---|---|---|---|---|---|
| colistin alone | 0.25 (0.25-2) | 2 | 16 | 0.25 (0.25-2) | 0.25 |
| colistin + DNM0650 (10 ug/ml) | ≤0.06 | nd | 1 | 0.25 | <0.06 |
| colistin + DNM0652 (10 ug/ml) | <0.06 | <0.06 | 0.25 | 0.25 | <0.06 |
| colistin + DNM0658 (10 ug/ml) | <0.06 | nd | 0.5 | 0.25 | <0.06 |
| colistin + DNM0693 (10 ug/ml) | 0.25 | nd | 2 | 0.5 | 0.25 |
| colistin + DNM0703 (10 ug/ml) | <0.06 | 2 | 2 | 0.25 | <0.06 |
| colistin + DNM0755 (10 ug/ml) | <0.06 | nd | 0.5 | 0.12 | <0.06 |
| colistin + DNM0760 (10 ug/ml) | nd | nd | nd | 0.06 | <0.06 |
| colistin + DNM0764 (10 ug/ml) | nd | nd | nd | 0.12 | <0.06 |

-continued

| Combination measured | E. coli ATCC 25922 | Klebsiella pneumoniae (Colistin Sensitive) MMX214 | Klebsiella pneumoniae (Colistin Resistant) MMX8390 | Pseudomonas aeurginosa ATCC 27853 | Acinetobacter Baumannii ATCC 19606 |
|---|---|---|---|---|---|
| colistin + DNM0650 (1 ug/ml) | <0.06 | 2 | 2 | 0.25 | 0.25 |
| colistin + DNM0652 (1 ug/ml) | <0.06 | 2 | 2 | 0.25 | <0.06 |
| colistin + DNM0658 (1 ug/ml) | <0.06 | 2 | 2 | 0.25 | <0.06 |
| colistin + DNM0693 (1 ug/ml) | 0.5 | nd | 16 | 0.5 | 0.5 |
| colistin + DNM0703 (1 ug/ml) | <0.06 | 8 | 8 | 0.25 | <0.06 |
| colistin + DNM0755 (1 ug/ml) | 0.12 | nd | 16 | 0.25 | <0.06 |

Many antibacterial adjuvant compounds at 10 ug/ml or 1 ug/ml resulted in improvement in the colistin MIC. Notably, the presence of antibacterial adjuvant compounds allowed colistin to regain significant activity against colistin-resistant strains.

The invention claimed is:

1. A compound, or a pharmaceutically acceptable salt thereof, of Formula I:

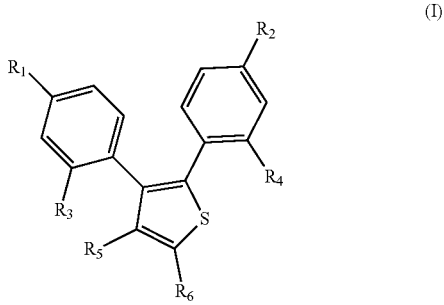

(I)

in which $R_1$ and $R_2$ are each independently fluoro or chloro; $R_3$ and $R_4$ are each independently alkyl; $R_5$ is hydrogen or alkyl; and $R_6$ is amide, sulfonamide or —$C(CF_3)_2OH$.

2. The compound of claim 1 in which $R_3$ and $R_4$ are each independently methyl, ethyl, or isopropyl.

3. The compound of claim 1 in which $R_1$ and $R_2$ are each both chloro.

4. The compound of claim 1 in which $R_3$ and $R_4$ are both methyl.

5. The compound of claim 1 in which $R_3$ and $R_4$ are both isopropyl.

6. The compound of claim 1 in which the compound is selected from compounds exemplified herein.

7. A method of treatment of a microbial infection comprising administering an effective amount of an antimicrobial compound of claim 1 to a patient in need thereof.

8. The method of treatment of claim 7 in which the microbial infection is substantially caused by Gram-positive bacteria.

9. The method of treatment of claim 8 in which the microbial infection comprises Staphylococcal infection.

10. The method of treatment of claim 8 in which the microbial infection comprises Enterococcal infection.

11. The method of treatment of claim 8 in which the microbial infection comprises *Bacillus* infection.

12. The method of treatment of claim 8 in which the microbial infection is substantially caused by a bacterial species selected from *Staphylococcus aureus*, *Staphylococcus epidermidis*, *Enterococcus faecalis*, *Enterococcus faecium*, *Bacillus cereus*, and *Streptococcus* sp.

13. A method of treatment of a microbial infection comprising administering an effective amount of an antimicrobial adjuvant compound of claim 1 and an effective amount of an antimicrobial compound to a patient in need thereof.

14. The method of treatment of claim 13 in which the microbial infection is substantially caused by Gram-negative bacteria.

15. The method of treatment of claim 13 in which the microbial infection is substantially caused by Gram-positive bacteria.

16. The method of treatment of claim 13 in which the microbial infection is polymicrobial.

17. The method of treatment of claim 13 in which the microbial infection is substantially caused by a bacterial species selected from *Pseudomonas aeruginosa*, *Klebsiella pneumoniae*, *Actinetobacter baumanii*, and *E. coli*.

18. The method of treatment of claim 13 in which the antimicrobial adjuvant compound is a compound of claim 1.

19. The method of treatment of claim 13 in which the antimicrobial compound is selected from the group consisting of colistin, ampicillin, erythromycin, and azithromycin.

20. A pharmaceutical composition comprising a compound of claim 1 and a pharmaceutically acceptable excipient.

21. The compound of claim 1 in which R1 and R2 are both chloro, R3 and R4 are both methyl, R5 is hydrogen, and R6 is —C(CF3)2OH.

22. The compound of claim 1 in which R1 and R2 are both chloro, R3 and R4 are both methyl, R5 is hydrogen, and R6 is sulfonamide.

* * * * *